United States Patent
Lee et al.

(10) Patent No.: US 8,487,106 B2
(45) Date of Patent: Jul. 16, 2013

(54) PROCESS FOR PREPARATION OF 2-METHYL-2'-PHENYLPROPIONIC ACID DERIVATIVES AND NOVEL INTERMEDIATE COMPOUNDS

(71) Applicant: Yuhan Corporation, Seoul (KR)

(72) Inventors: Chun-Ho Lee, Seoul (KR); Ja-Heouk Khoo, Gyeonggi-do (KR); Kyoung-Chan Kwon, Gyeonggi-do (KR); Hyun Ju, Gyeonggi-do (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 13/726,932

(22) Filed: Dec. 26, 2012

(65) Prior Publication Data

US 2013/0116439 A1    May 9, 2013

Related U.S. Application Data

(62) Division of application No. 12/865,234, filed as application No. PCT/KR2009/000668 on Feb. 12, 2009, now Pat. No. 8,367,704.

(30) Foreign Application Priority Data

Feb. 12, 2008  (KR) .................. 10-2008-0012656
Sep. 12, 2008  (KR) .................. 10-2008-0090385

(51) Int. Cl.
*C07D 401/04* (2006.01)
*C07D 413/14* (2006.01)

(52) U.S. Cl.
USPC ............ 546/199; 548/300.1; 558/52; 560/55; 560/103

(58) Field of Classification Search
USPC .. 514/315, 322; 546/199; 548/300.1; 558/52; 560/55, 103
See application file for complete search history.

(56) References Cited

U.S. PATENT DOCUMENTS

| 5,877,187 A | 3/1999 | Orjales et al. |
| 6,348,597 B2 | 2/2002 | Krauss et al. |
| 8,367,704 B2 * | 2/2013 | Lee et al. ............ 514/315 |

FOREIGN PATENT DOCUMENTS

| CN | 1176964 | 3/1998 |
| CN | 1603291 | 4/2005 |
| EP | 0079545 | 5/1983 |
| EP | 0580541 | 1/1994 |
| EP | 0818454 | 1/1998 |

OTHER PUBLICATIONS

Bhattacharyya, J., et al.; "Photodecomposition of an Acaricide, Fenazaquin, in Aqueous Alcoholic Solution;" J. Agric. Food Chem.; vol. 51, No. 14; dated May 15, 2003; pp. 4013-4016.
Database Registry [online], Registry No. 1000536-33-3 [retrieved on Aug. 21, 2009]. Retrieved from Registry Database, STN-International, Karlsruhe (DE), source: chemical catalog from Rare Chemicals GmbH, entered STN: Jan. 23, 2008 *structure of the compound with Registry No. 1000536-33-3*.
Database Registry [online], Registry No. 948552-52-1 [retrieved on Aug. 21, 2009]. Retrieved from: Registry Database, STN-International, Karlsruhe (DE), source: chemical library from APAC Pharmaceutical, LLC, entered STN: Sep. 28, 2007 *structure of the compound with Registry No. 948552-52-1*.
Iemura, R., et al.; "Synthesis of 2-(4-substituted-1-piperazinyl)benzimidazoles as H1-antihistaminic agents;" J. Med. Chemistry; vol. 29, No. 7; dated 1986; pp. 1178-1183.
Iemura, R., et al.; "Synthesis of benzimidazole derivatives as potential H1-antihistaminic agents;" J. Heterocyclic Chem.; vol. 24, No. 1; dated 1987; pp. 31-37.
International Search Report and Written Opinion for International Application No. PCT/KR2009/000668, mailed Sep. 18, 2009.
Office Action for Chinese Application No. 200980105040.X; dated Nov. 23, 2012.

* cited by examiner

*Primary Examiner* — Susanah Chung
(74) *Attorney, Agent, or Firm* — Alston & Bird LLP

(57) ABSTRACT

The present invention relates to a process for preparing 2-methyl-2'-phenylpropionic acid derivatives showing antihistamine activity in more simplified way, intermediate compounds and their preparation processes used therefore. According to the present invention, pharmaceutically useful 2-methyl-2'-phenylpropionic acid derivatives can be prepared with high yield and purity on industrial scale.

1 Claim, No Drawings

PROCESS FOR PREPARATION OF 2-METHYL-2'-PHENYLPROPIONIC ACID DERIVATIVES AND NOVEL INTERMEDIATE COMPOUNDS

This application is a divisional of U.S. application Ser. No. 12/865,234 filed Jul. 29, 2010, which is a national phase application and claims priority to PCT Application No. PCT/KR2009/000668 filed Feb. 12, 2009 that claims priority to Korean Application No. 10-2008-0012656 filed Feb. 12, 2008 and Korean Application No. 10-2008-0090385 filed Sep. 12, 2008, all of which are incorporated herein by reference in their entireties.

BACKGROUND OF THE INVENTION (a) Field of the Invention

The present invention relates to a process for preparing 2-methyl-2'-phenylpropionic acid derivatives, novel intermediate compounds and their preparation processes used therefore.

(b) Description of the Related Art 2-methyl-2'-phenylpropionic acid derivatives of the following Formula 1 show excellent antihistamine activity and antiallergic activity, and thus widely used in the field of pharmaceutics.

[Formula 1]

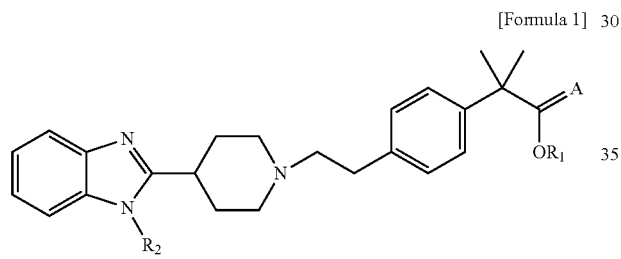

wherein, A is oxygen or nitrogen; $R_1$ is hydrogen or $C_1$-$C_6$ linear or branched alkyl when A is oxygen, and $R_1$ together with A forms a 5 to 7-membered ring unsubstituted or substituted with $C_1$-$C_6$ linear or branched alkyl when A is nitrogen; $R_2$ is hydrogen or —$CH_2CH_2OR_2'$, provided that $R_2$ is —$CH_2CH_2OR_2'$ when A is nitrogen; and $R_2'$ is hydrogen, $C_1$-$C_6$ linear or branched alkyl, $C_3$-$C_6$ cyclic alkyl, or $C_2$-$C_6$ alkenyl.

Particularly, 2-methyl-2'-phenylpropionic acid derivatives exclusively have $H_1$ antihistamine activity. Thus, they show high selectivity without acting with other pharmaceutical receptors even at higher dose. Therefore, 2-methyl-2'-phenylpropionic acid derivatives can be useful for a patient having allergic diseases, particularly for a patient who simultaneously receives other medicines, for example, those having cardiovascular disease (U.S. Pat. No. 5,877,187).

Meanwhile, EP 0818454 discloses a process for preparing 2-methyl-2'-phenylpropionic acid derivatives belong under the Formula 1. However, this process majorly has two disadvantages as follows.

First, preparation of an intermediate compound having oxaozle group introduced therein and hydrolysis of oxazole group are inevitably comprised in the process, making the whole process complicated. Second, in an another intermediate compound, N—H bonds capable of N-alkylation exist at imidazole group as well as piperidinyl group, and thus, plenty of by-products may be generated. Accordingly, the process is inefficient to obtain 2-methyl-2'-phenylpropionic acid derivatives of the Formula 1 on industrial scale.

Meanwhile, J. Med. Chemistry (1986, 29, 1178-1183) and J. Heterocyclic Chem. (1987, 24, 31-37) describes a process for preparing piperidinyl benzoimidazole derivatives. However, this process use highly inflammable zinc powder in the step of reducing nitro group to amine group, and the yield is very low as about 30%, thus inappropriate for industrial scale production.

For the above reasons, there still have been demands for improvement of yield or purity of pharmaceutically useful 2-methyl-2'-phenylpropionic acid derivatives and their preparation process suitable for industrial scale production.

SUMMARY OF THE INVENTION

Thus, the present invention is to provide a process for preparing 2-methyl-2'-phenylpropionic acid derivatives, which is suitable for industrial scale production of pharmaceutically useful 2-methyl-2'-phenylpropionic acid derivatives with higher yield.

Further, the present invention is to provide novel intermediate compounds that can be used in the preparation of 2-methyl-2'-phenylpropionic acid derivatives.

Moreover, the present invention is to provide a process for preparing the above intermediate compounds.

The present invention provides a process for preparing 2-methyl-2'-phenylpropionic acid derivatives of the following Formula 1, comprising the step of reacting a compound of the following Formula 2 with a compound of the following Formula 3:

[Formula 2]

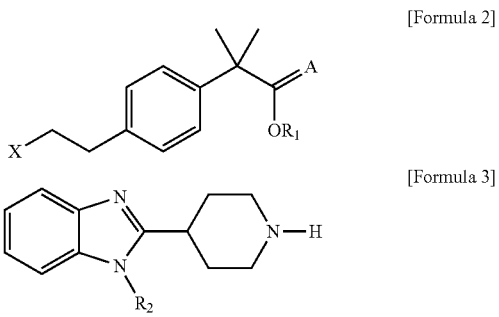

[Formula 3]

[Formula 1]

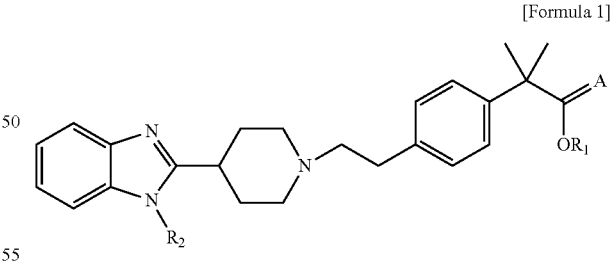

wherein, A is oxygen or nitrogen; $R_1$ is hydrogen or $C_1$-$C_6$ linear or branched alkyl when A is oxygen, and $R_1$ together with A forms a 5 to 7-membered ring unsubstituted or substituted with $C_1$-$C_6$ linear or branched alkyl when A is nitrogen; $R_2$ is hydrogen or —$CH_2CH_2OR_2'$, provided that $R_2$ is —$CH_2CH_2OR_2'$ when A is nitrogen; $R_2'$ is hydrogen, $C_1$-$C_6$ linear or branched alkyl, $C_3$-$C_6$ cyclic alkyl, or $C_2$-$C_6$ alkenyl; and X is a leaving group.

The present invention also provides a compound of the following Formula 1a, which may be used as an intermediate for preparing 2-methyl-2'-phenylpropionic acid derivatives:

[Formula 1a]

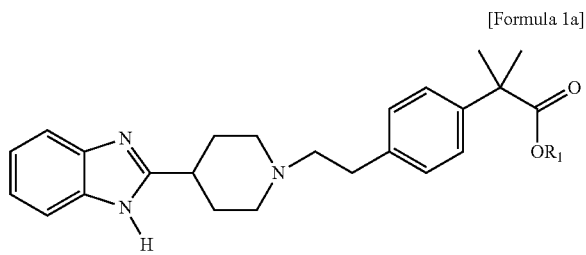

wherein $R_1$ is hydrogen or $C_1$-$C_6$ linear or branched alkyl.

Further, the present invention provides a compound of the following Formula 2a which may be used as an intermediate for preparing 2-methyl-2'-phenylpropionic acid derivatives, and the preparation thereof.

[Formula 2a]

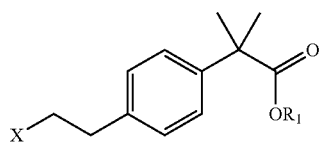

wherein $R_1$ is hydrogen or $C_1$-$C_6$ linear or branched alkyl, and X is a leaving group.

The present invention also provides a compound of the following Formula 6 which may be used as an intermediate for preparing 2-methyl-2'-phenylpropionic acid derivatives, and the preparation thereof.

[Formula 6]

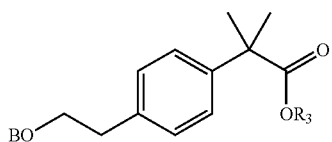

wherein $R_3$ is $C_1$-$C_6$ linear or branched alkyl, B is hydrogen or silyl protecting group.

The present invention also provides a novel process for preparing a compound of the following Formula 3a which may be used as an intermediate for preparing 2-methyl-2'-phenylpropionic acid derivatives:

[Formula 3a]

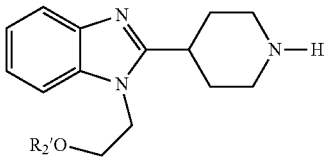

wherein $R_2$' is hydrogen, $C_1$-$C_6$ linear or branched alkyl, $C_3$-$C_6$ cyclic alkyl, or $C_2$-$C_6$ alkenyl.

DETAILED DESCRIPTION OF THE EMBODIMENTS

A process for preparing 2-methyl-2'-phenylpropionic acid derivatives, intermediate compounds and their preparation processes used therefore according to aspects of the present invention will now be explained in more detail.

In one aspect, a process for preparing 2-methyl-2'-phenyl-propionic acid derivatives of the following Formula 1 is provided. The process comprises the step of reacting a compound of the following Formula 2 with a compound of the following Formula 3:

[Formula 2]

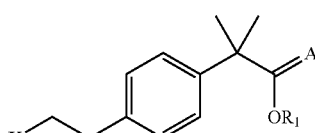

[Formula 3]

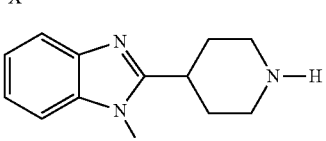

[Formula 1]

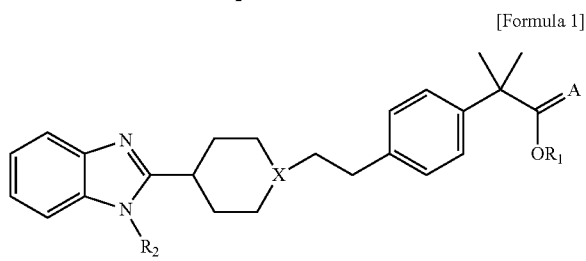

wherein, A is oxygen or nitrogen; $R_1$ is hydrogen or $C_1$-$C_6$ linear or branched alkyl when A is oxygen, and $R_1$ together with A forms a 5 to 7-membered ring unsubstituted or substituted with $C_1$-$C_6$ linear or branched alkyl when A is nitrogen; $R_2$ is hydrogen or —$CH_2CH_2OR_2$', provided that $R_2$ is —$CH_2CH_2OR_2$' when A is nitrogen; $R_2$' is hydrogen, $C_1$-$C_6$ linear or branched alkyl, $C_3$-$C_6$ cyclic alkyl, or $C_2$-$C_6$ alkenyl; and X is a leaving group.

In the above formulas, although not limited thereto, X may be a common leaving group suitable for reaction between the compound of the Formula 2 and the compound of the Formula 3, for example, halogen, sulfinyloxy group or sulfonyloxy group.

In this process, the compounds of the Formulas 2 and 3 can be reacted in the presence of a base in an organic solvent. As the base, for example, an inorganic base such as sodium $C_1$-$C_6$ alkoxide, potassium $C_1$-$C_6$ alkoxide, sodium carbonate, potassium carbonate, lithium carbonate, cesium carbonate, sodium bicarbonate, potassium bicarbonate, or potassium phosphate, or an organic base such as 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, dimethylaminopyridine or triethylamine can be used. Preferably, an inorganic base such as sodium $C_1$-$C_6$ alkoxide, potassium $C_1$-$C_6$ alkoxide, sodium carbonate, potassium carbonate, lithium carbonate, cesium carbonate, sodium bicarbonate, potassium bicarbonate, or potassium phosphate can be used. Thereby, reaction between the compounds of the Formulas 2 and 3 are preferably progressed to form a compound of the Formula 1.

Meanwhile, when $R_1$ of the Formula 1 is alkyl, after the reaction between the compounds of the Formulas 2 and 3, the reaction product can be ester-hydrolyzed to prepare 2-methyl-2'-phenylpropionic acid derivative of the Formula 1 in the form of an acid.

Further, when $R_2$ of the reaction product obtained by the reaction between the compounds of the Formulas 2 and 3 is hydrogen (for example, the reaction product is a compound of the following Formula 1a), if necessary, the reaction product can be reacted with a compound of the following Formula 9 to prepare 2-methyl-2'-henylpropionic acid derivative of the Formula 1.

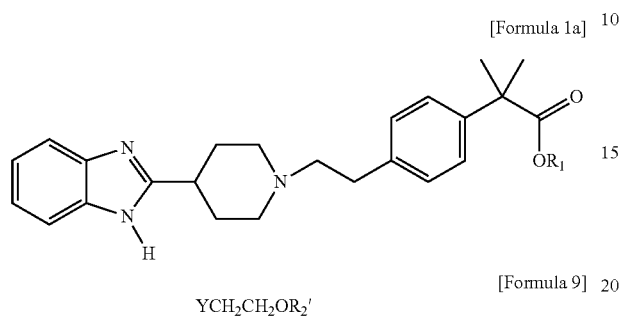

[Formula 1a]

YCH$_2$CH$_2$OR$_2$'

[Formula 9]

wherein $R_1$ is hydrogen or $C_1$-$C_6$ linear or branched alkyl, $R_2$' is hydrogen, $C_1$-$C_6$ linear or branched alkyl, $C_3$-$C_6$ cyclic alkyl, or $C_2$-$C_6$ alkenyl, and Y is a leaving group.

In the process according one aspect of the present invention, the compound of the Formula 2 may be represented by the following Formula 2a wherein $R_1$ is hydrogen or $C_1$-$C_6$ linear or branched alkyl when A is oxygen, or represented by the following Formula 2b wherein $R_1$ together with A forms a 5 to 7-membered ring unsubstituted or substituted by $C_1$-$C_6$ linear or branched alkyl when A is nitrogen.

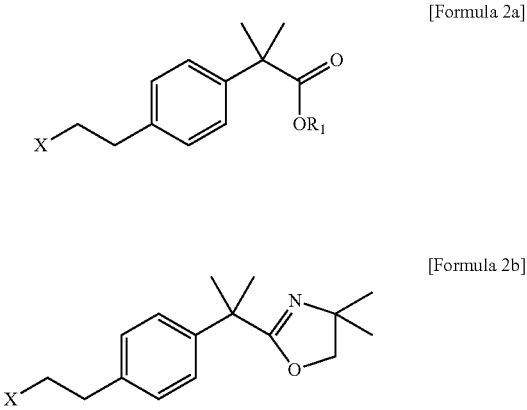

[Formula 2a]

[Formula 2b]

wherein $R_1$ is hydrogen or $C_1$-$C_6$ linear or branched alkyl, and X is a leaving group.

The compound of the Formula 2b can be easily prepared by a process publicly known in the art (see European Patent No. 0818454). Different from this compound, the compound of the Formula 2a is a novel intermediate compound useful for the preparation of 2-methyl-2'-phenylpropionic acid derivatives. Using this novel intermediate compound, 2-methyl-2'-phenylpropionic acid derivatives of the Formula 1 can be prepared in a more simplified process with high yield.

The compound of the Formula 2a can be prepared by substituting —OB group in a novel intermediate compound of the following Formula 6 with a leaving group X:

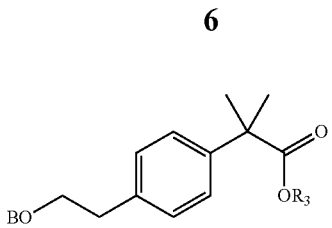

[Formula 6]

wherein $R_3$ is $C_1$-$C_6$ linear or branched alkyl, and B is hydrogen or silyl protecting group.

Further, the compound of the following Formula 6 can be prepared by reacting a compound of the following Formula 4 with a compound of the following Formula 5.

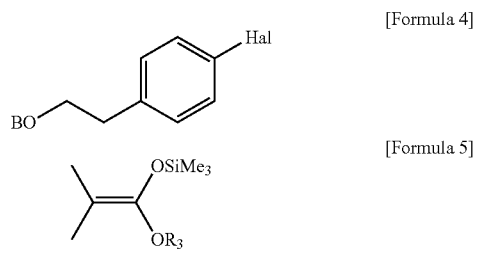

[Formula 4]

[Formula 5]

wherein Hal is halogen, $R_3$ is $C_1$-$C_6$ linear or branched alkyl, and B is hydrogen or silyl protecting group.

In the process, the compounds of the Formulas 4 and 5 are commercially available.

The compounds of the Formulas 4 and 5 can be reacted in the presence of Pd catalyst in an organic solvent. As the Pd catalyst, Pd(0) catalyst such as Pd(dba)$_2$, Pd$_2$(dba)$_3$ or Pd(t-Bu$_3$P)$_2$ can be used, and Pd(dba)$_2$ is preferable.

When B of the Formula 4 is hydrogen, if necessary, before the reaction of the compound of the Formula 4 and the compound of the Formula 5, a silyl protecting group can be introduced in the compound of the Formula 4. After that, the compound of the Formula 4 having the silyl protecting group introduced therein can be reacted with the compound of the Formula 5.

The silyl protecting group can be selected from the group consisting of hexamethyldisilyl, trimethylsilyl, tert-butyldimethylsilyl, triisopropylsilyl and tert-butyldiphenylsilyl. Preferably, hexamethyldisilyl, trimethylsilyl or tert-butyldimethylsilyl can be introduced.

And, if necessary, the compound of the Formula 6 which is prepared by the reaction of the compound of the Formula 4 having silyl protecting group introduced therein and the compound of the Formula 5 can be used in a subsequent reaction after deprotection of the silyl protecting group.

After the formation of the compound of the Formula 6, —OB group in the compound of the Formula 6 is substituted with the leaving group X to form the compound of the Formula 2a.

The leaving group X can be a common leaving group suitable for the reaction with the compound of the Formula 3, for example, halogen, sulfinyloxy group, or sulfonyloxy group. Thus, under common substitution reaction conditions according to the kinds of the leaving group, —OB group of the compound of the Formula 6 can be substituted with the leaving group X to obtain the compound of the Formula 2a. For example, in case the leaving group X is halogen, the compound of the Formula 6 can be reacted with common halogenation reagents to obtain the compound of the Formula 2a; and in case the leaving group X is sulfinyloxy or sulfonyloxy group, the compound of the Formula 6 can be reacted with common sulfinylation or sulfonylation reagents (for example, sulfinyl halide or sulfonyl halide) to obtain the compound of the Formula 2a.

In the preparation process of the compound of the Formula 2a, in the case where $R_1$ in the compound of the Formula 2a and $R_3$ in the compound of the Formula 6 are different to each other, if necessary, $R_3$ of the Formula 6 can be substituted with $R_1$, and then substitution with the leaving group X can be conducted to obtain the compound of the Formula 2a.

For example, in case $R_1$ is hydrogen, the compound of the Formula 2a can be obtained from the compound of the Formula 6 through ester-hydrolysis before the substitution with the leaving group X.

And, in case $R_1$ and $R_3$ are respectively different $C_1$-$C_6$ alkyl, the compound of the Formula 2a can be obtained from the compound of the Formula 6 through alkylation to substitute $R_3$ with $R_1$, or alternatively ester-hydrolysis and subsequent re-alkylation, before the substitution with the leaving group X.

Meanwhile, the compound of the Formula 3 may be preferably represented by the following Formula 3a wherein $R_2$ is —$CH_2CH_2OR_2'$.

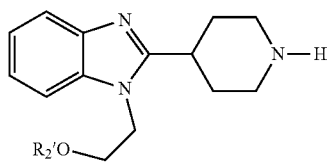

[Formula 3a]

wherein $R_2'$ is hydrogen, $C_1$-$C_6$ linear or branched alkyl, $C_3$-$C_6$ cyclic alkyl, or $C_2$-$C_6$ alkenyl.

According to the process of the present invention, the compound of the above Formula 3a can be prepared in a more simplified process. More specifically, the compound of the Formula 3a can be prepared by the steps of: protecting amine group of piperidine ring in a compound of the following Formula 7 with a protection group to form a compound of the following Formula 8; N-alkylating the compound of the Formula 8 with a compound of the following Formula 9 to form a compound of the following Formula 10; and deprotecting the compound of the Formula 10:

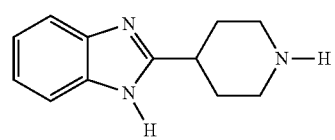

[Formula 7]

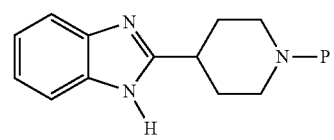

[Formula 8]

YCH₂CH₂OR₂'

[Formula 9]

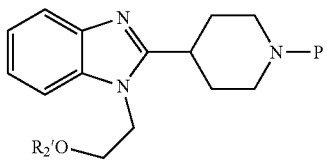

[Formula 10]

wherein P is an amine protecting group; $R_2'$ is hydrogen, $C_1$-$C_6$ linear or branched alkyl, $C_3$-$C_6$ cyclic alkyl, or $C_2$-$C_6$ alkenyl; and Y is a leaving group.

In the Formulas, the leaving group Y can be a common leaving group suitable for N-alkylation, for example, halogen, sulfinyloxy group or sulfonyloxy group.

In the process, the compound of the Formula 7 is commercially available.

Further, an amine protecting group (P) is introduced in the compound of the above Formula 7 in an organic solvent or aqueous solvent to form the compound of the above Formula 8. The amine protecting group P that can be used includes, without limitation, carbamate, amide, and silyl group, etc., and preferably carbamate.

The N-alkylation of the compound of the Formula 8 with the compound of the Formula 9 can be conducted in the presence of a base in an organic solvent. As the base, an inorganic base such as sodium hydroxide, potassium hydroxide, sodium $C_1$-$C_6$ alkoxide, potassium $C_1$-$C_6$ alkoxide, sodium carbonate, potassium carbonate, lithium carbonate, cesium carbonate, sodium bicarbonate, potassium bicarbonate, or potassium phosphate, or an organic base such as 1,8-diazabicyclo[5.4.0]undec-7-ene(DBU), 1,4-diazabicyclo[2.2.2]octane(DABCO), 1,5-diazabicyclo[4.3.0]non-5-ene (DBN), pyridine, dimethylaminopyridine or triethylamine can be used. Preferably, an inorganic base such as sodium hydroxide, potassium hydroxide, sodium $C_1$-$C_6$ alkoxide, potassium $C_1$-$C_6$ alkoxide, sodium carbonate, potassium carbonate, lithium carbonate, cesium carbonate, sodium bicarbonate, potassium bicarbonate, or potassium phosphate can be used.

As explained, after the formation of the compound of the Formula 10, it is deprotected to prepare the compound of the Formula 3a. Commonly used amine deprotection method and conditions can be applied for the deprotection.

Meanwhile, It is pharmaceutically preferable that 2-methyl-2'-phenylpropionic acid derivative of the Formula 1 prepared by the above method is 2-[4-(2-{4-[1-(2-ethoxy-ethyl)-1H-benzoimidazol-2-yl]-piperidin-1-yl}-ethyl)-phenyl]-2-methyl-propionic acid.

According to the preparation process of the 2-methyl-2'-phenylpropionic acid derivatives as explained, pharmaceutically useful 2-methyl-2'-phenylpropionic acid derivatives, which show excellent antihistamine activity, can be obtained with higher yield and purity in a more simplified process.

Accordingly, the process of the present invention is very efficient and appropriate for industrial scale production of the pharmaceutically useful 2-methyl-2'-phenylpropionic acid derivatives, and thus can raise pharmaceutical and industrial usefulness of the 2-methyl-2'-phenylpropionic acid derivatives.

The present invention is further explained in more detail with reference to the following examples. These examples, however, should not be interpreted as limiting the scope of the present invention in any manner.

Example 1

Preparation of 2-[4-(2-hydroxy-ethyl)-phenyl]-2-methyl-propionic acid methylester In a reaction vessel, 4-bromo phenethyl alcohol (2.0 g), Pd(dba)$_2$ (0.11 g), t-Bu$_3$P (0.08 g), ZnF$_2$ (0.52 g), methyltrimethylsilyl dimethylketene acetal (2.6 g) and DMF (20 mL) were introduced, and the mixture was reacted at 80□ for 18 hours. Distilled water (50 mL) and ethyl acetate (50 mL) were added thereto, and the mixture was stirred to separate layers. The separated organic layer was dehydrated with Na$_2$SO$_4$, and then condensed by filtration, and purified to obtain 2-[4-(2-hydroxy-ethyl)-phenyl]-2-methyl-propionic acid methylester (2.4 g, yield 100%).
$^1$H-NMR, 400 MHz, CDCl$_3$, ppm: δ 1.57 (s, 6H), 2.82-2.84 (t, 2H), 3.65 (s, 3H), 3.83-3.86 (t, 2H), 7.18-7.20 (d, 2H), 7.27-7.29 (d, 2H)

Example 2

Preparation of 2-[4-(2-hydroxy-ethyl)-phenyl]-2-methyl-propionic acid methylester In a reaction vessel, 4-bromo phenethyl alcohol (2 g), Pd$_2$(dba)$_3$ (0.18 g), t-Bu$_3$P (0.16 g), ZnF$_2$ (0.51 g), methyltrimethylsilyl dimethylketene acetal (2.6 g) and DMF (20 mL) were introduced, and the mixture was reacted at 80□ for 18 hours. Distilled water (50 mL) and ethylacetate (50 mL) were added thereto, and the mixture was stirred to separate layers. The separated organic layer was dehydrated with Na$_2$SO$_4$, and then condensed by filtration, and purified to obtain 2-[4-(2-hydroxy-ethyl)-phenyl]-2-methyl-propionic acid methylester (2.2 g, yield 94%).
$^1$H-NMR, 400 MHz, CDCl$_3$, ppm: δ 1.57 (s, 6H), 2.82-2.84 (t, 2H), 3.65 (s, 3H), 3.83-3.86 (t, 2H), 7.18-7.20 (d, 2H), 7.27-7.29 (d, 2H)

Example 3

Preparation of 2-[4-(2-hydroxy-ethyl)-phenyl]-2-methyl-propionic acid methylester In a reaction vessel, 4-bromo phenethyl alcohol (5.0 g), hexamethyldisilizane (HMDS; 3.0 g), acetonitrile (25 mL) and ammoniumchloride (0.01 g) were introduced, and the mixture was stirred at room temperature for 1 hours or more. The mixture was condensed under reduced pressure, and dichloromethane (30 mL) and distilled water (20 mL) were added to separate layers. The separated organic layer was dehydrated with Na$_2$SO$_4$, and then, condensed by filtration. And then, Pd(dba)$_2$ (0.29 g), t-Bu$_3$P (0.20 g), ZnF$_2$ (1.28 g), methyltrimethylsilyl dimethylketene acetal (2.2 g) and DMF (50 mL) were added thereto, and the mixture was reacted at 80□ for 18 hours. Distilled water (75 mL), ethylacetate (75 mL) and 1N hydrochloric acid (9 mL) were added thereto, and the mixture was stirred to separate layers. The separated organic layer was dehydrated with Na$_2$SO$_4$, and then condensed by filtration, and purified to obtain 2-[4-(2-hydroxy-ethyl)-phenyl]-2-methyl-propionic acid methylester (5.2 g, yield 88%).
$^1$H-NMR, 400 MHz, CDCl$_3$, ppm: δ 1.57 (s, 6H), 2.82-2.84 (t, 2H), 3.65 (s, 3H), 3.83-3.86 (t, 2H), 7.18-7.20 (d, 2H), 7.27-7.29 (d, 2H)

Example 4

Preparation of 2-[4-(2-hydroxy-ethyl)-phenyl]-2-methyl-propionic acid ethylester In a reaction vessel, 4-bromo phenethyl alcohol (2.0 g), Pd(dba)$_2$ (0.11 g), t-Bu$_3$P (0.08 g), ZnF$_2$ (0.52 g), ethyltrimethylsilyl dimethylketene acetal (2.7 g) and DMF (20 mL) were introduced, and the mixture was reacted at 80□ for 18 hours. Distilled water (50 mL) and ethylacetate (50 mL) were added thereto, and the mixture was stirred to separate layers. The separated organic layer was dehydrated with Na$_2$SO$_4$, and then condensed by filtration, and purified to obtain 2-[4-(2-hydroxy-ethyl)-phenyl]-2-methyl-propionic acid ethylester (2.3 g, yield 92%).
$^1$H-NMR, 400 MHz, CDCl$_3$, ppm: δ 1.25 (t, 3H), 1.57 (s, 6H), 2.82-2.84 (t, 2H), 4.10-4.45 (q, 2H), 3.83-3.86 (t, 2H), 7.18-7.20 (d, 2H), 7.27-7.29 (d, 2H)

Example 5

Preparation of 2-[4-(2-methanesulfonyloxy-ethyl)-phenyl]-2-methyl-propionic acid methylester In a reaction vessel, 2-[4-(2-hydroxy-ethyl)-phenyl]-2-methyl-propionic acid methylester (2.2 g) prepared in the Examples 1-3, triethylamine (1.2 g), methanesulfonylchloride (1.25 g) and dichloromethane (20 mL) were introduced, and the mixture was reacted at room temperature for 2 hours. Distilled water (50 mL) was added thereto, and the mixture was stirred to separate layers. The separated organic layer was dehydrated Na$_2$SO$_4$, and then condensed by filtration to obtain 2-[4-(2-methanesulfonyloxy-ethyl)-phenyl]-2-methyl-propionic acid methylester (3.2 g, yield 100%).
$^1$H-NMR, 400 MHz, CDCl$_3$, ppm: δ 1.57 (s, 6H), 2.86 (s, 3H), 3.02 (t, 2H), 3.65 (s, 3H), 4.39-4.43 (t, 2H), 7.19-7.21 (d, 2H), 7.28-7.30 (d, 2H)

Example 6

Preparation of 2-methyl-2-{4-[2-(toluene-4-sulfonyloxy)-ethyl]-phenyl}-propionic acid methylester In a reaction vessel, 2-[4-(2-hydroxy-ethyl)-phenyl]-2-methyl-propionic acid methylester (2 g) prepared in the Examples 1-3, triethylamine (1.1 g), p-toluenesulfonylchloride (1.9 g) and dichloromethane (20 mL) were introduced, and the mixture was reacted at room temperature for 1 hour. Distilled water (50 mL) was added thereto, and the mixture was stirred to separate layers. The separated organic layer was dehydrated with Na$_2$SO$_4$, and then condensed by filtration to obtain 2-methyl-2-{4-[2-(toluene-4-sulfonyloxy)-ethyl]-phenyl}-propionic acid methylester (3.0 g, yield 91%).
$^1$H-NMR, 400 MHz, CDCl$_3$, ppm: δ 1.57 (s, 6H), 2.44 (s, 3H), 2.93 (t, 2H), 3.65 (s, 3H), 4.18 (t, 2H), 7.05-7.07 (d, 2H), 7.19-7.21 (d, 2H), 7.27-7.30 (d, 2H), 7.69 (d, 2H)

Example 7

Preparation of 2-[4-(2-chloro-ethyl)-phenyl]-2-methyl-propionic acid methylester In a reaction vessel, 2-[4-(2-hydroxy-ethyl)-phenyl]-2-methyl-propionic acid methylester (1 g) prepared in the Examples 1-3, thionyl chloride (2.7 g) and dichloromethane (15 mL) were introduced, and the mixture was reacted at room temperature for 2 hours. Toluene (30 mL) was added, the mixture was condensed under reduced pressure, and the solvent was removed. Dichloromethane (50 mL) and sodium hydrogen carbonate solution (30 mL) were added thereto, and the mixture was stirred to separate layers. The separated organic layer was dehydrated with $Na_2SO_4$, and then condensed by filtration to obtain 2-[4-(2-chloro-ethyl)-phenyl]-2-methyl-propionic acid methylester (1.0 g, yield 92%).

$^1$H-NMR, 400 MHz, $CDCl_3$, ppm: δ 1.57 (s, 6H), 3.03-3.06 (t, 2H), 3.65 (s, 3H), 3.67-3.72 (t, 2H), 7.17-7.19 (d, 2H), 7.28-7.30 (d, 2H)

Example 8

Preparation of 2-[4-(2-methansulfonyloxy-ethyl)-phenyl]-2-methyl-propionic acid ethylester In a reaction vessel, 2-[4-(2-hydroxy-ethyl)-phenyl]-2-methyl-propionic acid ethylester (2.2 g) prepared in the Example 4, triethylamine (1.2 g), methanesulfonylchloride (1.25 g) and dichloromethane (20 mL) were introduced, and the mixture was reacted at room temperature for 2 hours. Distilled water (50 mL) was added thereto, and the mixture was stirred to separate layers. The separated organic layer was dehydrated with $Na_2SO_4$, and then condensed by filtration to obtain 2-[4-(2-methanesulfonyloxy-ethyl)-phenyl]-2-methyl-propionic acid ethylester (3.2 g, yield 100%).

$^1$H-NMR, 400 MHz, $CDCl_3$, ppm: δ 1.57 (s, 6H), 2.86 (s, 3H), 3.02 (t, 2H), 3.65 (s, 3H), 4.39-4.43 (t, 2H), 7.19-7.21 (d, 2H), 7.28-7.30 (d, 2H)

Example 9

Preparation of 2-{1-[4-(2-chloro-ethyl)-phenyl]-1-methyl-ethyl}-4,4-dimethyl-4,5-dihydro-oxazole In a reaction vessel, 2-[4-(2-hydroxy-ethyl)-phenyl]-2-methyl-propionic acid ethylester (25 g) prepared in the Example 4 and dichloromethane (200 mL) were introduced, and then 2-amino-2-methyl-1-propanol (10.6 mL) was introduced, and potassium t-butoxide (11.9 g) was slowly introduced. After the reaction was completed, distilled water (100 mL) was introduced to separate a layer, and the organic layer was condensed under reduced pressure. To the condensed organic layer, acetonitrile (150 mL) was added, and thionyl chloride (16 mL) was added dropwise, and then, the mixture was stirred to complete the reaction. After the reaction was completed, the mixture was cooled and sodium hydroxide solution was slowly added thereto to control pH from 5 to 7. Then, an organic solvent was removed by condensation, distilled water (150 mL) and dichloromethane (150 mL) were added thereto to separate layers. The separate organic layer was condensed under reduced pressure to obtain 2-{1-[4-(2-chloro-ethyl)-phenyl]-1-methyl-ethyl}-4,4-dimethyl-4,5-dihydro-oxazole (22.5 g, yield 80%).

$^1$H-NMR, 400 MHz, $CDCl_3$, ppm: 1.27 (s, 6H), 1.57 (s, 6H), 3.07 (t, 2H), 3.69 (t, 2H), 3.85 (s, 2H), 7.18 (d, 2H), 7.32 (d, 2H)

Example 10

Preparation of 4-(1H-benzoimidazol-2-yl)-piperidine-1-carboxylic acid tert-butyl ester In a reaction vessel, benzoimidazole (1.1 g) and methylalcohol (8 mL) were introduced, and di tert-butyldicarbonate (1.2 g) was added thereto. The mixture was stirred at room temperature for about 3 hours, and then the mixture was condensed to obtain 4-(1H-benzoimidazol-2-yl)-piperidine-1-carboxylic acid tert-butyl ester (1.5 g, yield 91%).

$^1$H-NMR, 400 MHz, $CDCl_3$, ppm: 1.63 (s, 9H), 1.89 (m, 2H), 2.11 (d, 2H), 2.87 (t, 2H), 3.14 (m, 1H), 4.23 (s, 2H), 7.22-7.24 (m, 2H), 7.41 (s, 1H), 7.72 (s, 1H), 9.77 (s, 1H)

Example 11

Preparation of 4-[1-(2-ethoxyethyl)-1H-benzoimidazol-2-yl]-piperidine-1-carboxylic acid tert-butyl ester In a reaction vessel, 4-(1H-benzoimidazol-2-yl)-piperidine-1-carboxylic acid tert-butyl ester (1.5 g) prepared in the Example 10, toluene (10 mL) and potassium hydroxide (0.8 g) were introduced, and temperature of the mixture was controlled to 50° C. or more. To the mixture, ethoxyethanol methane sulfonate (1.3 g) was added, and then, it was stirred at the same temperature until the reaction was completed. After the reaction was completed, distilled water (10 mL) was added to separate layers, and then an organic layer was condensed to obtain 4-[1-(2-ethoxyethyl)-1H-benzoimidazol-2-yl]-piperidine-1-carboxylic acid tert-butyl ester (1.7 g, 91%).

$^1$H-NMR, 400 MHz, $CDCl_3$, ppm: 1.07 (t, 3H), 1.47 (s, 9H), 1.92 (m, 2H), 2.01 (s, 2H), 2.85 (s, 2H), 3.14 (m, 1H), 3.36 (m, 2H), 3.69 (t, 2H), 4.28 (t, 2H), 7.12-7.26 (m, 3H), 7.75 (t, 1H)

Example 12

Preparation of 1-(2-ethoxyethyl)-2-piperidin-4-yl-1H-benzoimidazole

In a reaction vessel, 4-[1-(2-ethoxyethyl)-1H-benzoimidazol-2-yl]-piperidine-1-carboxylic acid tert-butyl ester (1.6 g) prepared in the Example 11, distilled water (15 mL) and hydrochloric acid (1.5 g) were introduced, and then the mixture was stirred to conduct deprotection. And then, sodium hydroxide solution (10 mL) and dichloromethane (20 mL) were added thereto. An organic layer was separated and condensed to obtain 1-(2-ethoxyethyl)-2-piperidin-4-yl-1H-benzoimidazole (1.2 g, 100%).

$^1$H-NMR, 400 MHz, $CDCl_3$, ppm: 1.05 (t, 3H), 2.09-2.23 (m, 4H), 3.17 (q, 2H), 3.24 (d, 1H), 3.39 (q, 2H), 3.51 (q, 3H), 3.77 (t, 2H), 4.51 (t, 2H), 7.27 (m, 2H), 7.52 (d, 1H), 7.62 (d, 1H)

Example 13

Preparation of 2-(4-{2-[4-(1H-benzoimidazol-2-yl)-piperidin-1-yl]-ethyl}-phenyl)-2-methyl-propionic acid methylester In a reaction vessel, 2-[4-(2-methanesulfonyloxy-ethyl)-phenyl]-2-methyl-propionic acid methylester (3.0 g) prepared in the Example 5, sodium carbonate (1.1 g), 2-(4-piperadinyl)-1H-benzoimidazole (3.0 g) and methylalcohol (30 mL) were introduced, and the mixture was reacted for 14 hours under reflux condition. Distilled water (50 mL) was added to crystallize. The crystals were filtered under reduced pressure, washed with distilled water, and dried to obtain 2-(4-{2-[4-(1H-benzoimidazol-2-yl)-piperidin-1-yl]-ethyl}-phenyl)-2-methyl-propionic acid methylester (3.4 g, yield 85%).

$^1$H-NMR, 400 MHz, DMSO, ppm: 1.48 (s, 6H), 1.80-1.84 (m, 2H), 1.98-2.00 (m, 2H), 2.08-2.13 (t, 2H), 2.50-2.54 (m, 1H), 2.67-2.75 (t, 2H), 2.80-2.90 (m, 1H), 3.01-3.04 (d, 2H), 7.05-7.08 (m, 2H), 7.13-7.23 (d, 4H), 7.46 (s, 2H), 12.15 (s, 1H)

Example 14

Preparation of 2-[4-(2-{4-[1-(2-ethoxy-ethyl)-1H-benzoimidazol-2-yl]-piperidin-1-yl}-ethyl)-phenyl]-2-methyl-propionic acid methylester In a reaction vessel, 2-(4-{2-[4-(1H-benzoimidazol-2-yl)-piperidin-1-yl]-ethyl}-phenyl)-2-methyl-propionic acid methylester (0.5 g) prepared in the Example 13, potassium-t-butoxide (0.14 g), ethoxyethylmesylate (0.25 g) and DMF (20 mL) were introduced, and the mixture was reacted at 50□ for 3 hours. Distilled water (50 mL) and ethylacetate (50 mL) were added thereto, and the mixture was stirred to separate a layer. Separated organic layer was washed with distilled water (50 mL), dehydrated, and condensed under reduced pressure to obtain 2-[4-(2-{4-[1-(2-ethoxy-ethyl)-1H-benzoimidazol-2-yl]-piperidin-1-yl}-ethyl)-phenyl]-2-methyl-propionic acid methylester (0.5 g, yield 85%, HPLC purity 98.5% or more).

$^1$H-NMR, 400 MHz, DMSO, ppm: 0.98 (t, 3H), 1.48 (s, 6H), 1.87 (m, 4H), 2.05-2.20 (m, 2H), 2.50 (t, 2H), 2.73 (t, 2H), 3.04 (m, 3H), 3.30 (q, 2H), 3.58 (s, 3H), 3.65 (t, 2H), 4.39 (t, 2H), 7.00-7.30 (m, 6H), 7.40-7.60 (dd, 2H)

Example 15

Preparation of 2-[4-(2-{4-[1-(2-ethoxy-ethyl)-1H-benzoimidazol-2-yl]-piperidin-1-yl}-ethyl)-phenyl]-2-methyl-propionic acid ethylester In a reaction vessel, 2-[4-(2-methanesulfonyloxy-ethyl)-phenyl]-2-methyl-propionic acid ethylester (3.2 g) prepared in the Example 8, sodium carbonate (1.1 g), 1-(2-ethoxy-ethyl)-2-piperidin-4-yl-1H-benzoimidazole (3.0 g) prepared in the Example 12 and methylalcohol (30 mL) were introduced, and the mixture was reacted for 14 hours under reflux condition. Distilled water (50 mL) was added thereto, and the mixture was stirred and crystallized. The crystals were filtered under reduced pressure, and washed with distilled water, and then dried to obtain 2-[4-(2-{4-[1-(2-ethoxy-ethyl)-1H-benzoimidazol-2-yl]-piperidin-1-yl}-ethyl)-phenyl]-2-methyl-propionic acid ethylester (4.5 g, yield 90%, HPLC purity 98.5% or more).

$^1$H-NMR, 400 MHz, CDCl$_3$, ppm: 1.12 (t, 3H), 1.56 (s, 6H), 2.12 (m, 2H), 2.18 (m, 4H), 2.63 (q, 2H), 2.81 (q, 2H), 3.00 (m, 1H), 3.16 (d, 2H), 3.42 (q, 2H), 3.74 (t, 2H), 4.15 (q, 2H), 4.33 (t, 2H), 7.15-7.40 (m, 7H), 7.77 (q, 1H)

Example 16

Preparation of 2-[4-(2-{4-[1-(2-ethoxy-ethyl)-1H-benzoimidazol-2-yl]-piperidin-1-yl}-ethyl)-phenyl]-2-methyl-propionic acid In a reaction vessel, 2-[4-(2-{4-[1-(2-ethoxy-ethyl)-1H-benzoimidazol-2-yl]-piperidin-1-yl}-ethyl)-phenyl]-2-methyl-propionic acid methylester (2.3 g) prepared in the Example 14, sodium hydroxide (0.6 g) and ethylalcohol (13 mL) were introduced, and the mixture was reacted at 50-55□ for 3 hours. Distilled water (20 mL) was added thereto, and acetic acid was added to control the pH to 7. Ethylacetate (50 mL) was added thereto, and the mixture was stirred to separate a layer. The separated organic layer was condensed under reduced pressure. And, butanol (9 mL) was added thereto, and dissolved by heating. And then, it was cooled to precipitate crystals, and the crystals were filtered under reduced pressure to obtain 2-[4-(2-{4-[1-(2-ethoxy-ethyl)-1H-benzoimidazol-2-yl]-piperidin-1-yl}-ethyl)-phenyl]-2-methyl-propionic acid (2.0 g, yield 90%, HPLC purity 99% or more).

$^1$H-NMR, 400 MHz, CDCl$_3$, ppm: δ 1.08 (t, 3H), 1.59 (s, 6H), 2.15-2.30 (m. 4H), 2.64-2.79 (m, 6H), 3.25 (s, 1H), 3.67 (q, 2H), 3.47 (m, 2H), 3.71 (t, 2H), 4.32 (t, 2H), 6.79 (d, 2H), 7.26 (m, 2H), 7.29-7.32 (m, 3H), 7.76 (t, 1H)

Example 17

Preparation of 2-[4-(2-{4-[1-(2-ethoxy-ethyl)-1H-benzoimidazol-2-yl]-piperidin-1-yl}-ethyl)-phenyl]-2-methyl-propionic acid In a reaction vessel, 2-[4-(2-{4-[1-(2-ethoxy-ethyl)-1H-benzoimidazol-2-yl]-piperidin-1-yl}-ethyl)-phenyl]-2-methyl-propionic acid ethylester (2.3 g) prepared in the Example 15, sodium hydroxide (0.6 g) and ethyl alcohol (13 mL) were introduced, and the mixture was reacted at 50-55□ for 3 hours. Distilled water (20 mL) was added thereto, and acetic acid was added to control the pH to 7. Ethylacetate (50 mL) was added thereto, and the mixture was stirred to separate layers. The separated organic layer was condensed under reduced pressure. And, butanol (9 mL) was added and dissolved by heating. And then, it was cooled to precipitate crystals, and the crystals were filtered under reduced pressure to obtain 2-[4-(2-{4-[1-(2-ethoxy-ethyl)-1H-benzoimidazol-2-yl]-piperidin-1-yl}-ethyl)-phenyl]-2-methyl-propionic acid (1.84 g, yield 85%, HPLC purity 99% or more).

$^1$H-NMR, 400 MHz, CDCl$_3$, ppm: δ 1.08 (t, 3H), 1.59 (s, 6H), 2.15-2.30 (m. 4H), 2.64-2.79 (m, 6H), 3.25 (s, 1H), 3.67 (q, 2H), 3.47 (m, 2H), 3.71 (t, 2H), 4.32 (t, 2H), 6.79 (d, 2H), 7.26 (m, 2H), 7.29-7.32 (m, 3H), 7.76 (t, 1H)

Example 18

Preparation of 2-[1-(2-{4-[1-(4,4-dimethyl-4,5-dihydro-oxazol-2-yl)-1-methyl-ethyl]-phenyl}-ethyl)-piperidin-4-yl]-1-(2-ethoxy-ethyl)-1H-benzoimidazole In a reaction vessel, 2-{1-[4-(2-chloro-ethyl)-phenyl]-1-methyl-ethyl}-4,4-dimethyl-4,5-dihydro-oxazole (1.9 g) prepared in the Example 9, sodium carbonate (0.8 g), 1-(2-ethoxyethyl)-2-piperidin-4-yl-1H-benzoimidazole (2.0 g) prepared in the Example 12 and methyl alcohol (20 mL) were introduced, and the mixture was reacted for 14 hours under reflux condition to obtain 2-[1-(2-{4-[1-(4,4-dimethyl-4,5-dihydro-oxazol-2-yl)-1-methyl-ethyl]-phenyl}-ethyl)-piperidin-4-yl]-1-(2-ethoxy-ethyl)-1H-benzoimidazole (4.4 g, yield 87%, HPLC purity 98% or more).

$^1$H-NMR, 400 MHz, CDCl$_3$, ppm: 1.10 (t, 3H), 1.27 (s, 6H), 1.57 (s, 6H), 1.92 (m, 2H), 2.10 (m, 4H), 2.60 (t, 2H), 2.80 (t, 2H), 3.01 (m, 1H), 3.10 (d, 2H), 3.41 (q, 2H), 3.70 (t, 2H), 3.90 (s, 2H), 4.30 (t, 2H), 7.10-7.32 (m, 7H), 7.8 (m, 1H)

Example 19

Preparation of 2-[4-(2-{4-[1-(2-ethoxy-ethyl)-1H-benzoimidazol-2-yl]-piperidin-1-yl}-ethyl)-phenyl]-2-methyl-propionic acid In a reaction vessel, 2-[1-(2-{4-[1-(4,4-dimethyl-4,5-dihydro-oxazol-2-yl)-1-methyl-ethyl]-phenyl}-ethyl)-piperidin- 4-yl]-1-(2-ethoxy-ethyl)-1H-benzoimidazole (4.4 g) prepared in the Example 18 and hydrochloric acid aqueous solution (50 mL) were introduced, and the mixture was stirred with reflux. After the reaction was completed, sodium hydroxide solution was added to control the pH to 7. Ethylacetate (50 mL) was added to separate a layer, and the organic layer was condensed under reduced pressure. And, butanol (9 mL) was added and dissolved by heating. And then, it was cooled to precipitate crystals, and the crystals were filtered under reduced pressure to obtain 2-[4-(2-{4-[1-(2-ethoxy-ethyl)-1H-benzoimidazol-2-yl]-piperidin-1-yl}-ethyl)-phenyl]-2-methyl-propionic acid (3.43 g, yield 87%, HPLC purity 99% or more).

$^1$H-NMR, 400 MHz, CDCl$_3$, ppm: δ 1.08 (t, 3H), 1.59 (s, 6H), 2.15-2.30 (m. 4H), 2.64-2.79 (m, 6H), 3.25 (s, 1H), 3.67 (q, 2H), 3.47 (m, 2H), 3.71 (t, 2H), 4.32 (t, 2H), 6.79 (d, 2H), 7.26 (m, 2H), 7.29-7.32 (m, 3H), 7.76 (t, 1H)

What is claimed is:
1. A compound of the following Formula 1a:

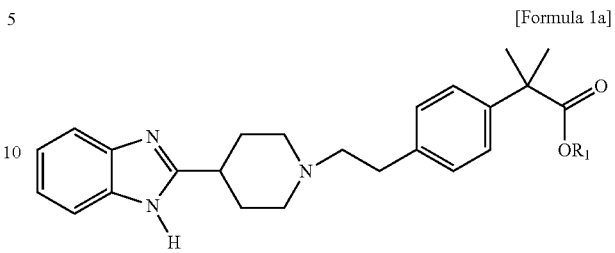

[Formula 1a]

wherein $R_1$ is hydrogen or $C_1$-$C_6$ linear or branched alkyl.

* * * * *